United States Patent [19]

Flamand et al.

[11] 3,995,473
[45] Dec. 7, 1976

[54] INSPECTION HEAD

[75] Inventors: Guy Flamand, Champforgeuil; Alain Billoud, Chalon-sur-Saone, both of France

[73] Assignee: Carnaud Total Interplastic, Chalon-sur-Saone, France

[22] Filed: July 11, 1975

[21] Appl. No.: 595,124

[30] Foreign Application Priority Data

July 15, 1974 France .................. 74.24742

[52] U.S. Cl. ................... 73/49.2; 73/94
[51] Int. Cl.² ........................ G01M 3/26
[58] Field of Search ........ 73/40, 41, 49.2, 49.3, 73/37, 94

[56] References Cited

UNITED STATES PATENTS

| | | | |
|---|---|---|---|
| 3,771,649 | 11/1973 | Strauss | 73/94 |
| 3,805,594 | 4/1974 | Hayashi | 73/37 |
| 3,832,892 | 9/1974 | Bohl | 73/94 |

*Primary Examiner*—Donald O. Woodiel
*Attorney, Agent, or Firm*—Pennie & Edmonds

[57] ABSTRACT

An inspection head to test objects such as plastic bottles for absence of leaks and crushing resistance includes a column having a seal for an aperture in the object which may be applied to the object to exert a crushing force and a fluid supply source to apply a pressure inside the object, which pressure is compared with a reference pressure by means of a movable diaphragm. When the object has an adequate resistance to crushing so that the column does not move beyond a certain point, and the object is free from leaks so that the difference in pressure does not exceed a given value, apertures in sliding members movable according to the positions of the diaphragm and column are in alignment, which fact may be checked by passing a light beam through the apertures. When the apertures are not in alignment the object may be rejected. The head may be used for continuous in-line inspection of objects which are produced successively.

8 Claims, 1 Drawing Figure

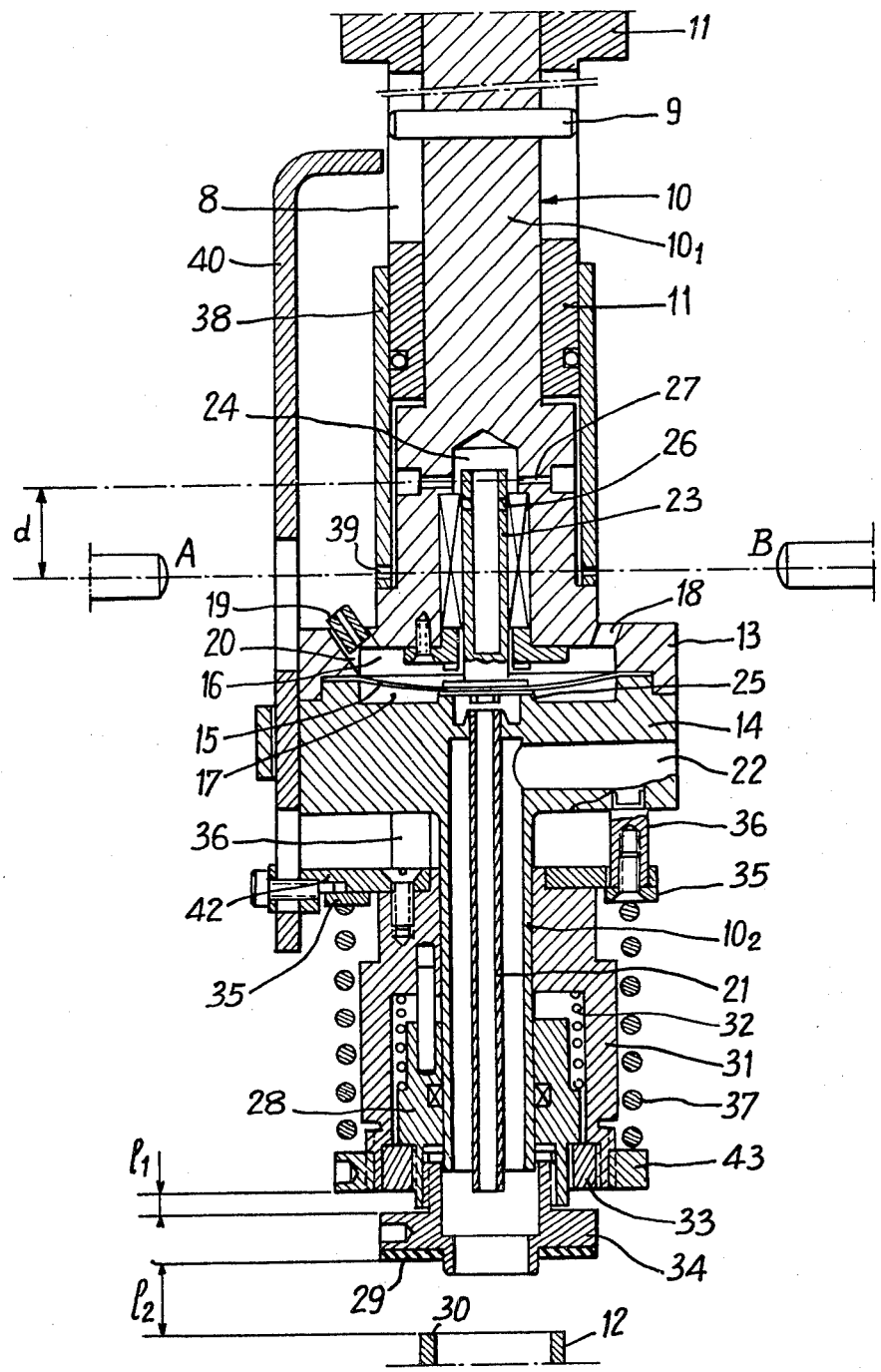

INSPECTION HEAD

BACKGROUND OF THE INVENTION

This invention relates to an inspection head for hollow objects such as plastics bottles which can be used for detecting, firstly, leakages due for example to minute holes in the hollow body walls or to a ring defect, such as lack of planeity and secondly, an insufficient vertical crushing strength due for example to incorrect distribution of the material of the wall of the object or to an overall lack of weight in the object, regardless of the method of manufacture of the object, for example by extrusion-blowmoulding, by injection-blowmoulding, or by any other method.

PRIOR ART

Various devices are known for detecting minute leaks by means of over-pressure or by sub-pressure, but hitherto there has not been known any device capable of simultaneously and continuously testing for the presence of minute holes and for the correct distribution of the material in bottles.

DESCRIPTION OF THE INVENTION

According to one aspect of the invention there is provided an inspection head for verifying absence of leakage and resistance to crushing of a hollow object which comprises:

a fixed frame having a vertically slidable tubular column mounted thereon, the column being provided with a first diametral passage, means for supporting a hollow object and on the longitudinal axis of the column, a sealing component fixed to the lower end of the column capable of sealingly engaging a mouth of the object around an aperture in the object, elastic means between the column and the sealing component arranged to urge the sealing component towards the mouth when the column descends towards and makes contact with the object, to maintain the sealing component in contact with the mouth after contact therewith, and to exert a crushing force of predetermined magnitude on the object, when the column continues to descend after contact, a deformable diaphragm, fixed in the tubular column in a plane transverse to the direction of sliding of the column, means for subjecting the upper face of the diaphragm to a predetermined first fluid pressure, means for subjecting the lower face of the diaphragm and also the interior of the object to a predetermined second fluid pressure exceeding said predetermined first pressure, a vertical rod supported by and projecting upwardly from the diaphragm and traversed by a second diametral passage positioned to become aligned with the first passage when said predetermined second pressure is applied, a tubular slider mounted to slide vertically on said fixed frame and provided with a third diametral passage aligned with the first diametral passage in a normal operative position of the tubular slider, and an entraining element movable with said elastic means and capable of lowering the slider and hence bringing the third passage out of alignment with the first and second passages if the object collapses after contact between its mouth and the sealing component.

In this specification, including the claims, the inspection device according to the invention is described with the column movable vertically and with the object to be tested vertically below the column. It should however be understood that the invention includes such a head when mounted in any other attitude, and when the column may move along a path which is not vertical, the operation of the head is the same whatever the attitude of the head.

The correct distribution of the material and the absence of leakage in the object under test are confirmed when, after the crushing force has been applied to the object and said first and second predetermined pressures have been applied to the diaphragm, the passage through the column and that through the rod come into alignment with the passage in the sliding sleeve. The alignment can be verified by the passage of a beam of light through the line of sight of the passages.

If the bottle is sufficiently strong against crushing but is perforated, the passage through the vertical rod does not become located in alignment with the passage through the column, and the beam of light does not pass along the line of sight.

If the bottle is insufficiently strong against crushing, the aforementioned sleeve will be displaced downwards by the driving element, which may be formed by a hook, so that its passage will be located below the line of sight. Under these circumstances, even if the passage through the vertical rod and the passage through the column coincide, the beam of light will not be able to pass through.

DESCRIPTION OF PREFERRED EMBODIMENT

An embodiment of the invention will be described by way of example with reference to the accompanying drawing, of which the single FIGURE is a section of a device according to the invention applied to testing of a bottle.

The inspection device illustrated in the drawing comprises a central column 10, mounted for vertical sliding inside a fixed tubular portion of the frame 11. The column 10 is prevented from turning about its longitudinal axis by a pin 9, the ends of which can move in vertical grooves 8 provided in the frame 11. The column may be lowered, for example by means of a cam of conventional design, not shown in the drawing, towards the neck 12 of a bottle to be tested. The column comprises an upper portion $10_1$ and a tubular lower portion $10_2$, connected together by flanges 13, 14, between which flanges there is clamped the periphery of an elastic, pressure-sensitive diaphragm 15. This diaphragm is mounted in a chamber formed at the adjoining ends of the portions $10_1$ and $10_2$ and defines together with these portions an upper space 16 and a lower space 17. The pressure in the space 16 is maintained by continuously blowing in a fluid, such as air, through an orifice 18, and said pressure may be regulated to a predetermined value by means of a nozzle 19 mounted in an orifice 20 communicating with the space 16 and perforated by a narrow passage to constitute a controllable leak.

A long vertical pipe 21, coaxial with the tubular lower portion $10_2$, and the lower end of which is adapted to be introduced into the bottle 12 to be tested, leads into the space 17. The result is that, when the head is applied onto the bottle, as will be explained below, the space 17 communicates with the interior of the bottle through the intermediary of the pipe 21. The interior of the bottle also communicates, through the annular space between the pipe 21 and the lower portion $10_2$, with an orifice 22, to which is connected a pressure source of known type, not shown in the drawing.

In order that the fluid blown in through the orifice 22 shall not pass directly into the space 17 but shall first pass into the bottle, the orifice 22 is positioned as far as practicable from the lower end of the pipe 21. In this way, the pressure in the space 17 will be that which exists inside the bottle.

Onto the diaphragm there is fixed a vertical rod 23 arranged to move inside an internal bore 24 of the upper portion $10_1$ when the diaphragm 15 deforms. In its at-rest position, that is to say when the head is not applied onto the bottle, the diaphragm 15, which is subjected only to its own weight and to the weight of the rod, rests upon a seating 25.

The rod 23 is perforated by a diametral passage 26 which, when the diaphragm 15 occupies said at-rest position, is situated slightly below a diametral passage 27 passing through the upper portion $10_1$ of the column 10. The offsetting between the passages 26 and 27 and the size of the opening in the nozzle 19 are so designed that, when the inspection head is applied to a bottle free from any defects and the spaces 16 and 17 are pressurised, the passage 26 becomes located coaxial to the passage 27. With advantage, the spaces 16 and 17 may be supplied from a single pressure source.

At the lower end of the lower portion $10_2$ of the column there is sleeved-on an annular component 28, equipped with a sealing gasket 29 intended for ensuring a leak-tight contact between said annular component and the mouth 30 of the neck of the bottle. Around the lower portion $10_2$ there is slidably mounted a second annular component 31. The annular components 28 and 31 possess shoulders, against which there bears a relatively weak spring 32 intended for transmitting between the component 31 and the component 28 an axial force sufficient to maintain a sealing contact between the gasket 29 and the mouth 30. When the column descends, the spring 32 becomes compressed until a ring 33 carried on the component 31, and a ring 34 fixed to the component 28, come into contact with each other.

Between the ring 33 and an annular flange 35 carried by studs 36 integral with the column 10, there is disposed a relatively strong spring 37, intended for transmitting to the component 28 a crushing force for the bottle to be tested, when the column 10 continues to descend, after the rings 33 and 34 have come into contact with each other.

A tubular sliding sleeve 38, a portion of which projects onto the column 10, is telescopically slidably mounted around the tubular portion of the frame 11. The portion projecting onto the column is provided with a diametral passage 39 situated, when the head is raised, below the passage 27 through the column. The distance $d$ between the passage 27 and 39 should be slightly less than the sum of the distance $P_1$ between the rings 33 and 34 and the distance $P_2$ between the sealing gasket 29 and the mouth 30 of the bottle, so that in the position of coaxiality of the passages 27 and 39, the rings 33 and 34 are not in contact and the sealing gasket 29 is pressed against the mouth 30 only by the spring 32. As will be explained below, inspection of the bottles is carried out by bringing the passages 26 and 27 into coaxiality with the passage 39. This coaxiality can be verified when a beam of light A-B passes through the three passages.

A flange 42, integral with the annular component 31, carries a hook 40, the free end of which terminates above the upper edge of the sliding sleeve 38, at a distance slightly exceeding the offsetting $d$ defined above.

The method of functioning of the inspection head is as follows:

Initially, the head is situated in the position shown in the figure, that is to say it is separated from the bottle 12, the springs 32 and 37 being consequently unstressed. A pressure is applied permanently through the orifice 18, so that the diaphragm 15 rests upon its seating 25.

The column 10 is lowered far enough to bring its passage 27 below the line of sight A-B, formed by the passage 39 through the sliding sleeve 38, which remains stationary. The sealing gasket 29 now comes into contact with the mouth 30 of the neck of the bottle. At this instant, as a result of the stiffness of the spring 37, the descent of the column leads to compression of the weak spring 32, until contact is established between the ring 33 and the ring 34. From this instant onwards, a further lowering of the column 10 leads, provided that the bottle is sufficiently strong, to compression of the spring 37. The hook 40, which is integral with the flange 42, comes into the vicinity of the upper part of the sliding sleeve 38, without however coming into contact with it. The sliding sleeve is therefore not displaced, so that its passage 39 remains in the line of sight A-B.

In a second phase of the movement of the column, the column is raised, sufficiently for its passage 27 to become situated in the line of sight A-B. The spring 37 relaxes, re-establishing contact between the flange 42 and the flange 35, after which the rings 33 and 34 again move apart, that is to say the sealing gasket 29 is no longer pressed onto the mouth except by the spring 32. A pressure of a few millibars is then supplied through the orifice 22. If the bottle is not perforated, the pressure produced in the space comprised between the tubular portion $10_2$ and the pipe 21 is transmitted by this pipe to the lower space 17, whereas the pressure in the upper space 16 is regulated to be slightly lower, because of the slight escape provided through the nozzle 19. The passage 26 through the rod 23 now becomes situated coaxially to the passage 27.

Thus, if the sliding sleeve 38 has not been displaced during the course of the descent of the column 10, the three passages 39, 26 and 27 are aligned. The passing of the light beam A-B through these three passages then attests to the fact that the bottle is both sufficiently resistant to crushing and is also not perforated.

If, by contrast, the bottle is sufficiently resistant to crushing but is perforated, the passage 26 does not come opposite to the passage 27, when pressurised fluid is blown in through the orifice 22. The bottle is considered as faulty and is rejected by an automatic device of known type, not shown in the drawing.

Finally, in the case where the bottle is not perforated but is insufficiently resistant to crushing, the stiffness of the spring 37, which can be adjusted by the nut 43, will have permitted the hook 40, during the descent of the column 10, to come into contact with the sliding sleeve 38 and to lower the latter slightly, so that its passage 39 will have descended to below the line of sight A-B. At the instant of the re-ascent of the column 10, in spite of the coincidence of the passage 27 and possibly also the passage 26 with the line of sight, the light beam is not able to pass and the bottle will therefore be rejected.

The invention has been described above with respect to the inspection of bottles, but it may also of course be applied to the inspection of other hollow objects, especially of plastics or similar materials. It will be seen that testing for lack of crushing strength, which may be caused by incorrect distribution of the material of the walls, and leakages which may be caused by pin-holes, are carried out simultaneously. The device may be operated continuously so that a succession of similar objects are tested automatically.

I claim:
1. An inspection head for verifying absence of leakage and resistance to crushing of a hollow object which comprises:
    a fixed frame having a vertically slidable tubular column mounted thereon, the column being provided with a first diametral passage,
    means for supporting a hollow object below and on the longitudinal axis of the column,
    a sealing component fixed to the lower end of the column capable of sealingly engaging a mouth of the object around an aperture in the object,
    elastic means between the column and the sealing component arranged to urge the sealing component towards the mouth when the column descends towards and makes contact with the object, to maintain the sealing component in contact with the mouth after contact therewith, and to exert a crushing force of predetermined magnitude on the object, when the column continues to descend after contact,
    a deformable diaphragm, fixed in the tubular column in a plane transverse to the direction of sliding of the column, means for subjecting the upper face of the diaphragm to a predetermined first fluid pressure, means for subjecting the lower face of the diaphragm and also the interior of the object to a predetermined second fluid pressure exceeding said predetermined first pressure,
    a vertical rod supported by and projecting upwardly from the diaphragm and traversed by a second diametral passage positioned to become aligned with the first passage when said predetermined second pressure is applied,
    a tubular slider mounted to slide vertically on said fixed frame and provided with a third diametral passage aligned with the first diametral passage in a normal operative position of the tubular slider, and
    an entraining element movable with said elastic means and capable of lowering the slider and hence bringing the third passage out of alignment with the first and second passages if the object collapses after contact between its mouth and the sealing component.

2. An inspection head according to claim 1, in which the elastic means comprises an intermediate annular component slidably mounted around the column, a relatively weak spring bearing upon the sealing component and upon the intermediate component, a relatively strong spring arranged between the intermediate component and a seating integral with the column, the force exerted by the weak spring being sufficient to ensure a leak-tight contact between the sealing component and the mouth of the object, and means for adjusting the force exerted by the strong spring to produce the desired crushing force.

3. An inspection head according to claim 1, in which the column is composed of an upper part and of a tubular lower part connected together by means of flanges having hollow recesses, between which flanges there is clamped the periphery of the elastic diaphragm, the latter defining respectively, together with cavities formed in the adjoining ends of the upper and lower portions, an upper space having inlet means to receive fluid to supply said first predetermined pressure, and a lower space communicating with a duct within the lower part, the lower end of the duct being arranged to enter the interior of the object when the head is applied to the mouth of the object.

4. An inspection head according to claim 3, in which said duct is coaxial with said lower part.

5. An inspection head according to claim 3 having an orifice in the lower part of the column and means for supplying fluid to the orifice to provide said predetermined second pressure in the duct and the lower part of the column.

6. An inspection head according to claim 5, in which said orifice is provided at a point in the column remote from said lower end.

7. An inspection head according to claim 3, in which the upper space and the lower space are provided with a common source of fluid, and a nozzle is mounted in an orifice communicating with the upper space and having a narrow aperture to form an adjustable leak to maintain the difference between said first and second pressures at a desired value.

8. An inspection head according to claim 1, provided with a light source arranged to project a beam of light through said first, second and third passages when the passages are aligned with each other and means for detecting the beam after it has traversed the aligned passages.

* * * * *

UNITED STATES PATENT AND TRADEMARK OFFICE
CERTIFICATE OF CORRECTION

PATENT NO. : 3,995,473
DATED : December 7, 1976
INVENTOR(S) : Guy Flamand and Alain Billoud It is certified that error appears in the above-identified patent and that said Letters Patent are hereby corrected as shown below:

Under the caption "Foreign Application Priority Data",
July 15, 1974 should read --July 16, 1974.--

Column 1, line 33, "object and" should read --object below and--.

Column 3, line 59, "passage" should read --passages--.

Signed and Sealed this

Twenty-sixth Day of April 1977

[SEAL]

Attest:

RUTH C. MASON
Attesting Officer

C. MARSHALL DANN
Commissioner of Patents and Trademarks